United States Patent [19]

Nedelec et al.

[11] Patent Number: 4,774,242
[45] Date of Patent: Sep. 27, 1988

[54] TETRAHYDROBENZ(C,D)INDOLES AND PHARMACEUTICAL USE

[75] Inventors: Lucien Nedelec, Le Raincy; Claude Rettien, Montreuil-Sous-Bois; Claude Gueniau, Paris, all of France

[73] Assignee: Roussel Uclaf, Paris, France

[21] Appl. No.: 16,074

[22] Filed: Feb. 18, 1987

[30] Foreign Application Priority Data

Feb. 24, 1986 [FR] France ................. 86 02509

[51] Int. Cl.⁴ ............. A61K 31/535; C07D 498/06
[52] U.S. Cl. ................................ 514/229.5; 544/99
[58] Field of Search ...................... 544/99; 514/227

[56] References Cited

U.S. PATENT DOCUMENTS

| | | | |
|---|---|---|---|
| 4,238,486 | 12/1980 | Jones | 544/99 X |
| 4,313,944 | 2/1982 | Nedelec et al. | 544/99 X |
| 4,318,910 | 3/1982 | Nedelec et al. | 544/99 X |
| 4,493,836 | 1/1985 | Nedelec et al. | 544/99 X |
| 4,503,053 | 3/1985 | Nedelec et al. | 544/99 X |

*Primary Examiner*—Richard L. Raymond
*Attorney, Agent, or Firm*—Bierman and Muserlian

[57] ABSTRACT

Novel tetrahydrobenz[c,d]indoles of the formula

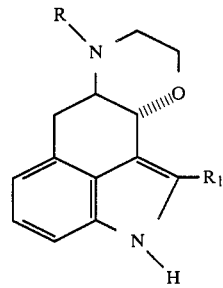

wherein R is selected from the group consisting of hydrogen, alkyl of 1 to 6 carbon atoms and cycloalkyl of 3 to 6 carbon atoms and $R_1$ is selected from the group consisting of hydrogen, chlorine and bromine and their non-toxic, pharmaceutically acceptable acid addition salts having antianoxic, hypotensive, antihypertensive and dopaminergic agonist activity.

19 Claims, No Drawings

TETRAHYDROBENZ(C,D)INDOLES AND PHARMACEUTICAL USE

STATE OF THE ART

Related U.S. patents are U.S. Pat. Nos. 4,493,836 and 4,318,910 and the art discussed in the latter.

OBJECTS OF THE INVENTION

It is an object of the invention to provide the novel compounds of formula I and their non-toxic, pharmaceutically acceptable acid addition salts and a process for their preparation.

It is another object of the invention to induce hypotensive, dopaminergic agonistic, antihypertensive and antianoxic activity in warm-blooded animals.

These and other objects and advantages of the invention will become obvious from the following detailed description.

THE INVENTION

The novel compounds of the invention are selected from the group consisting of tetrahydrobenz[c,d]indoles of the formula

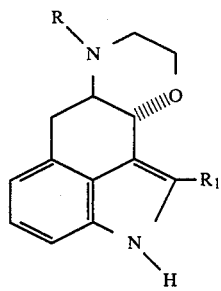

wherein R is selected from the group consisting of hydrogen, alkyl of 1 to 6 carbon atoms and cycloalkyl of 3 to 6 carbon atoms and $R_1$ is selected from the group consisting of hydrogen, chlorine and bromine and their non-toxic, pharmaceutically acceptable acid addition salts.

Examples of R are alkyl such as methyl, ethyl, n-propyl, isopropyl, n-butyl and isobutyl, cycloalkyl such as cyclopropyl, cyclopropylmethyl and cyclohexyl and hydrogen.

Exmples of suitable acids for the formation of the non-toxic, pharmaceutically acceptable acid addition salts are inorganic acids such as hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane or ethane sulfonic acid, arylsulfonic acids such as benzene or p-toluene sulfonic acid and arylcarboxylic acids.

Among the preferred compounds of formula I are those wherein $R_1$ represents a hydrogen atom.

Among these are the derivatives wherein R is alkyl of 1 to 6 carbon atoms or hydrogen and their acid addition salts. Specific preferred compounds are (d,l-trans) 2,6a,7,8,9,10a-hexahydro-7-propyl-6H-indolo[4,3-g,h]-1,4-benzoxazine and, (d,l-trans) 1-bromo-2,6a,7,8,9,10a-hexahydro-7-propyl-6H-indolo-[4,3-g,h]-1,4-benzoxazine and their non-toxic, pharmaceutically acceptable acid addition salts.

The novel process of the invention for the preparation of the compounds of formula I comprises reducing a compound of the formula

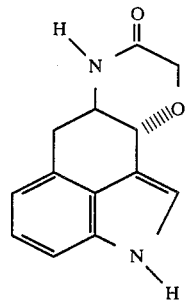

to obtain a compound of the formula

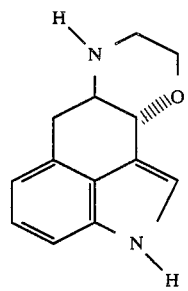

which may be optionally isolated and salified or reacted with an alkylation agent to obtain a compound of the formula

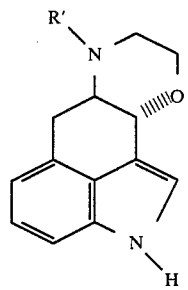

wherein R' is alkyl of 1 to 6 carbon atoms or cycloalkyl or cycloalkylalkyl of 3 to 6 carbon atoms which is optionally isolated and salified and optionally reacting compound of formula $I_A$ or $I_B$ with a halogenating agent to obtain a compound of the formula

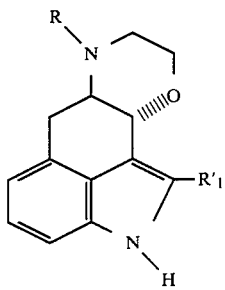

wherein R has the above definition and $R_1'$ is chlorine or bromine which is isolated and optionally salified.

In a preferred mode of the invention, the reduction is effected with a hydride such as aluminum lithium hydride and the alkylating agent is an alkyl halide, preferably the iodide, in the presence of a condensation agent such as an alkali metal carbonate or bicarbonate. For methylation, it is preferred to use formol in the presence of a reducing agent such as sodium or potassium borohydride or cyanoborohydride.

The halogenation agent for reaction with a compound of formula $I_B$ may be N-chlorosuccinimide or N-bromosuccinimide or the brominated complex of pyrrolidone of the formula

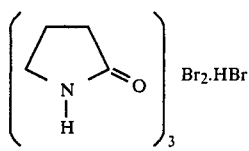

The compounds of formula II may be prepared by hydrogenating a compound of the formula

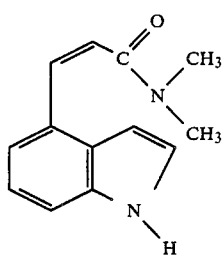   III to obtain a compound of the formula

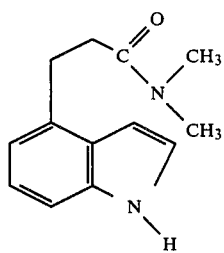   IV cyclizing the latter to form a compound of the formula

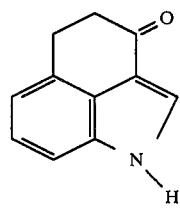   V brominating the latter to form a compound of the formula

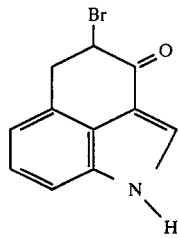   VI reacting the latter with an azide to obtain a compound of the formula

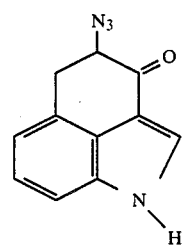   VII subjecting the latter to hydrogenation to obtain a compound of the formula

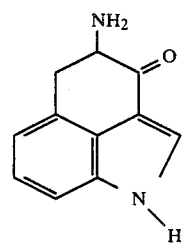   VIII reacting the latter with chloroacetyl chloride to obtain a compound of the formula

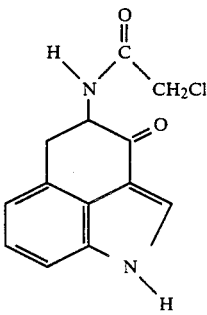   IX reducing the latter to obtain a compound of the formula

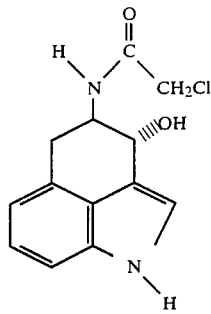

and cyclizing the latter to obtain a compound of formula II.

The reduction of 4-formylindole with triphenyl phosphonium N,N-dimethylacetamide chloride is preferably carried out with the usual conditions of a Wittig reaction. The hydrogenation of the derivative of formula III is preferably carried out in the presence of a catalyst such as palladium, platinum, or Raney's nickel and in a solvent such as an alkanol of low molecular weight like methanol or ethanol or in an inert solvent such as dioxane.

The cyclization of the derivative of formula IV is preferably done in the presence of phosphorus oxychloride and an alkaline hydrolysis is then carried out, for example with sodium hydroxide or preferably by aqueous ammonia.

The bromination of the derivative of formula V is preferably effected with bromine but reagents such as pyridinium perbromide or N-bromosuccinimide can also be used. The azide is preferably an alkali metal azide, preferably of sodium but other azides such as trimethylsilyl azide can also be used. The hydrogenation of the derivative of formula VII is preferably done in the same conditions as those used for the derivative of formula III.

The reaction of the compounds of formula VIII with chloroacetyl chloride is preferably effected in the presence of an acid binding agent, preferably sodium hydroxide, in an organic solvent such as dioxane or tetrahydrofuran and, preferably, chloroform. The reduction of the compounds of formula IX is preferably carried out with a hydride such as a cyanoborohydride, and particularly an alkali metal borohydride such as sodium borohydride. The cyclization of the compound of formula X is, for example, carried out with a strong base such as an alkali metal alcoholate such as sodium ethylate or sodium tert-butylate, but preferably with sodium hydride. It is advantageously done in an ether such as dioxane or tetrahydrofuran, but preferably in 1,2-dimethoxyethane.

The compounds of formula I have a basic character and the acid addition salts thereof can with advantage be prepared by reacting a mineral or organic acid in more or less stoichiometric proportions with the compounds of formula I. The salts can be prepared without isolating the corresponding bases.

The novel antianoxic, hypotensive, antihypertensive and dopaminergic agonist compositions of the invention are comprised of an effective amount of at least one compound of formula I and its non-toxic, pharmaceutically acceptable acid addition salts and an inert pharmaceutical carrier or excipient. The compositions may be in the form of tablets, dragees, capsules, granules, suppositories or injectable solutions or suspensions.

Examples of suitable excipients are talc, gum arabic, lactose, starch, magnesium stearate, cocoa butter, aqueous and non-aqueous vehicles, fatty substances of animal or vegetable origin, paraffin derivatives, glycols, various wetting, dispersing or emulsifying agents and preservatives.

The compositions of the invention possess very useful pharmacological properties; they are endowed in particular with remarkable dopaminergic agonist, hypotensive and antihypertensive properties. In addition, they are endowed with anti-anoxic properties.

They are useful in the treatment of neurological syndromes of extra-pyramidal origin, for example, in the treatment of Parkinson's disease and in the treatment of post-encephalitic parkinsonian syndromes. They can also be used in the treatment of essential arterial hypertensions, hypertension of fifty-year-olds, of menopause, of diabetics, the obese and the plethoric as well as in the treatment of arterial hypertension of the aged person or one attacked by arteriosclerosis, and in the treatment of hypertension of renal origin. They can also be used in the treatment of cerebral senescence or of manifestations connected with cerebral hypoxia.

Among the preferred compositions of the invention are those wherein R is hydrogen or alkyl of 1 to 6 carbon atoms and especially (d,l-trans) 2,6a,7,8,9.10a-hexahydro-7-propyl-6H-indol[4,3-g,h]-1,4-benzoxazine and its addition salts with pharmaceutically acceptable acids.

The novel method of the invention for inducing antianoxic, dopaminergic agonist and hypotensive activity in warm-blooded animals comprises administering to warm-blooded animals an antianoxically, hypotensively and dopaminergic agonistically effective amount of at least one compound of formula I and their non-toxic, pharmaceutically acceptable acid addition salts. The compounds can be administered orally, rectally or parenterally and the usual daily dose is 0.015 to 3 mg/kg depending on the specific compound, the condition treated and the method of administration. For example, the oral administration of 0.015 to 1.5 mg/kg of the product of Example 2 is useful for the treatment of cerebral senescence.

The compound of formula II is novel.

In the following examples there are described several preferred embodiments to illustrate the invention. However, it should be understood that the invention is not intended to be limited to the specific embodiments.

EXAMPLE 1

(E) 2,6a,7,10a-tetrahydro-6H-indo-[4,3-g,h]-benzoxazin-8(9H)-one

STEP A:

N,N-dimethyl-3-(1H-indol-4-yl)-2-propenamide 6 g of 4-formyl indole were stirred for 19 hours in 100 ml of tetrahydrofuran with the ylid corresponding to triphenylphosphonium N,N-dimethyl acetamide prepared as follows:

A solution of 15.6 g of triphenylphosphine and 6 g of 2-chloro-N,N-dimethylacetamide in 100 ml of nitromethane was refluxed for 19 hours and then evaporated to dryness. The residue was washed with isopropyl ether and dried under reduced pressure to obtain 21 g of colorless crystals, 11 g of which were dissolved in 10 ml of water. The solution was made alkaline with 2N sodium hydroxide and then extracted with methylene chloride. The extracts were dried, filtered and evaporated to dryness under reduced pressure to obtain the ylid sought.

After the 19 hours, the product was chromatographed over silica (eluent: cyclohexane-ethyl acetate 5-5) to obtain 7 g of N,N-dimethyl-3-(1-indol-4-yl)-2-propenamide melting at ≃185° C.

STEP B: N,N-dimethyl-1H-indol-4-propanamide 187 g of the product from Step A were hydrogenated for 4 hours and 30 minutes at normal pressure in 1.5 liters of ethanol in the presence of 9 g of palladium at 10% on activated charcoal followed by filtering and washing with 1 liter of chloroform, and evaporating to dryness under reduced pressure. The residue was triturated in ether, filtered and dried under reduced pressure to obtain 156.3 g of N,N-dimethyl-1H-indol-4-propanamide melting at ≃118° C.

STEP C: 4,5-dihydrobenz[c,d]indol-3-(1H)-one 50 g of the product of Step B were stirred for 3 hours at 70° C. under an inert atmosphere in 500 ml of tetrahydrofuran and 125 ml of phosphorus oxychloride. The mixture was then poured into 1.8 liters of 5N ammonia at 5° C. and was extracted with ethyl acetate. The extracts were washed with water, dried, evaporated to dryness under reduced pressure, and purified by chromatography over silica (eluent: cyclohexane-ethyl acetate 7-3) to obtain 19.2 g of 4,5-dihydrobenz[c,d]indol-3-(1H)-one melting at ≃184° C.

STEP D:
4-bromo-4,5-dihydrobenz[c,d]indol-3-(1H)-one

A solution of 5 g of product of Step C in 50 ml of tetrahydrofuran was cooled to −17° C. under an inert atmosphere and 50 ml of a 20% solution of bromine in tetrahydrofuran were added. The mixture was poured into 400 ml of water and then was extracted with methylene chloride. After drying, evaporating to dryness under reduced pressure and crystallizing from isopropyl ether, 5.4 g of 4-bromo-4,5-dihydrobenz[c,d]indol-3-(1H)-one melting at ≃210° C. were obtained.

STEP E: 4-azido-4,5-dihydrobenz[c,d]indol-3-(1H)-one

A solution of 6.7 g of sodium azide and 11.5 g of the product of Step D was stirred for 15 hours at 5° C. in 115 ml of dimethylformamide and then was poured into 500 ml of water. The product obtained was separated and purified by chromatography over silica (eluent: cyclohexane-ethyl acetate 5-5) to obtain 7 g of 4-azido-4,5-dihydrobenz[c,d]indol-3(1H)-one melting at ≃150° C. with decomposition.

STEP F: 4-amino-4,5-dihydrobenz[c,d]indol-3(1H)-one 6 g of product of Step E in 200 ml of ethanol were hydrogenated for 6 hours with stirring in the presence of 600 mg of palladium at 10% on activated charcoal. After filtering, washing with chloroform and evaporating the filtrate to dryness under reduced pressure, 6 g of 4-amino-4,5-dihydrobenz[c,d]indol-3(1H)-one melting at ≃225° C. were obtained.

STEP G:
2-chloro-N-(3-oxo-1,3,4,5-tetrahydrobenz[c,d]indol-4-yl)-acetamide 850 mg of the product of Step F, 39 ml of chloroform, 0.75 ml monochloroacetyl chloride and 10 ml of water were stirred for 30 minutes in an ice bath. After filtering, washing the crystallized product with water and drying it, 800 mg of 2-chloro-N-(3-oxo-1,3,4,5-tetrahydrobenz[c,d]indol-4-yl)-acetamide were obtained.

STEP H:
2-chloro-N-(3-hydroxy-1,3,4,5-tetrahydrobenz[c,d]indol-4-yl)-acetamide 800 mg of the product of Step G were stirred for 30 minutes in 8 ml of methanol and 8 ml of water with 400 mg of sodium borohydride. After extracting with ethyl acetate, washing the extracts with water, drying, evaporating to dryness under reduced pressure and purifying by chromatography over silica (eluent: ethyl acetate), 520 mg of 2-chloro-N-(3-hydroxy-1,3,4,5-tetrahydrobenz[c,d]indol-4-yl)-acetamide were obtained.

STEP I: (E) 2,6a,7,10a-tetrahydro-6H-indol-[4,3-g,h]-1,4-benzoxazin-8-(9H)-one 1.5 g of the product of Step H in 30 ml of 1,2-dimethoxyethane were stirred for 30 minutes in an ice bath with 330 mg of sodium hydride at 55% in oil and then a further 330 mg of sodium hydride were added after 2 hours 30 minutes. Then, 200 ml go water were carefully added, followed by filtering, washing with water, separating, and drying under reduced pressure to obtain 900 mg of (E) 2,6a,7,10a-tetrahydro-6H-indol-[4,3-g,h]-1,4-benzoxazin-8-(9H)-one melting at >260° C.

UV Spectrum:

| Max | 221 nm | $E_1^1 = 1,422$ | $\epsilon = 32,500$ |
| Max | 272 nm | $E_1^1 = 260$ | $\epsilon = 5,900$ |
| Max | 279 nm | $E_1^1 = 263$ | $\epsilon = 6,000$ |
| Max | 290 nm | $E_1^1 = 216$ | $\epsilon = 4,900$ |
| Infl | 320, 330, 360 nm | | |

EXAMPLE 2

(dl-trans) 2,6,6a,7,8,9,10a-hexahydro-6H-indol-[4,3-g,h]-1,4-benzoxazine and its (E) 2-butene dioate (2:1)

Under an inert atmosphere, 1.4 g of (E) 2,6a,7,10a-tetrahydro-6H-indolo-[4,3-g,h]-1,4-benzoxazin-8(9H)-one and 700 mg of aluminum-lithium hydride in 15 ml of tetrahydrofuran were stirred at 60° C. for 4 hours and 5 ml of tetrahydrofuran hydrated to 10% were added with cooling. After extraction with methylene chloride, the extracts were dried, evaporated to dryness under reduced pressure and purified by chromatography over silica (eluent: methylene chloride-methanol 9-1) to obtain 540 mg of (dl-trans) 2,6,6a,7,8,9.10a-hexahydro-6H-indol-[4,3-g,h]-1,4-benzoxazine.

Formation of the (E) 2-butene dioate (2:1)

60 ml of methanol were added to 1 g of the said base, and after filtering, 290 mg of fumaric acid were added. Then, 50 ml of ethyl acetate were added followed by separating and recrystallizing from methanol to obtain 850 mg of the (E) 2-butene dioate melting at ≃255° C.

UV Spectrum (methanol+dimethylsulfoxide)

| Max | 273 nm | $E_1^1 = 254$ | $\epsilon = 6,900$ |
| Max | 279 nm | $E_1^1 = 259$ | $\epsilon = 7,050$ |
| Max | 289–290 nm | $E_1^1 = 206$ | $\epsilon = 5,600$ |

EXAMPLE 3

(dl-trans) 2,6a,7,8,9,10a-hexahydro-7-propyl-6H-indol-[4,3-g,h]-1,4-benzoxazine and its (E) butene dioate (2:1)

Under an inert atmosphere, 439 mg of the base of Example 2, 4 ml of dimethylformamide, 553 mg of potassium carbonate and 1 ml of propyl iodide were stirred for 1 hour at 50° C. and the mixture was poured into 50 ml of water and extracted with ethyl acetate. The extracts were dried and evaporated to dryness under reduced pressure to obtain 412 mg of (dl-trans) 2,6a,7,8,9,10a-hexahydro-7-propyl-6H-indol-[4,3-g,h]-1,4-benzoxazine.

Formation of the (E) butene dioate (2:1

The said base was dissolved in 5 ml of methanol and 93 mg of fumaric acid and 20 ml of ethyl acetate were added. After concentrating to about 5 ml and separating, 300 mg of (dl-trans) 2,6a,7,8,9,10a-hexahydro-7-propyl-6H-indol-[4,3-g,h]-1,4-benzoxazine (E) butene dioate melting at ≃260° C. were obtained.

UV Spectrum (Ethanol HCl 0.1N)

| Max | 220 nm | $E_1^1 = 1,268$ | $\epsilon = 39,900$ |
| Max | 272 nm | $E_1^1 = 191$ | $\epsilon = 6,000$ |
| Max | 278 nm | $E_1^1 = 195$ | $\epsilon = 6,100$ |
| Max | 290 nm | $E_1^1 = 160$ | $\epsilon = 5,000$ |

EXAMPLE 4

(d,l trans) 2,6a,7,8,9,10a-hexahydro-7-methyl 6H-indol-[4,3-g,h]-1,4-benzoxazine and its hydrochloride Under an inert atmosphere, 1 g of base of Example 2 was stirred for 1 hour with 4 ml of 40% formaldehyde, 20 ml of methanol and 950 mg of sodium cyanoborohydride. 50 ml of water were added and extraction was effected with ethyl acetate. The extracts were dried and evaporated to dryness under reduced pressure to obtain 900 mg of (d,l trans) 2,6a,7,8,9,10a-hexahydro-7methyl 6H-indol-[4,3-g,h]-1,4-benzozazine.

The said base was salified in the form of the hydrochloride, then recrystallized from methanol to obtain 700 mg of the hydrochloride melting at ≃260° C.

UV Spectrum (ethanol HCl)

| Max | 220 nm | $E_1^1 = 1,279$ | $\epsilon = 36,600$ |
| Max | 220 nm | $E_1^1 = 212$ | $\epsilon = 6,100$ |
| Max | 279 nm | $E_1^1 = 222$ | $\epsilon = 6,350$ |
| Max | 282 nm | $E_1^1 = 205$ | |
| Max | 290 nm | $E^1 = 181$ | $\epsilon = 5,200$ |

EXAMPLE 5

Tablets were prepared containing 2 mg of the (E) butene dioate of (d,l-trans) 2,6a,7,8,9,10a-hexahydro-7-propyl-6H-indolo-[4,3-g,h]-1,4-benzoxazine or 10 mg of (d,l-trans) 2,6a,7,8,9,10a-hexahydro-7-methyl-6H-indolo-[4,3-g,h]-1,4-benzoxazine hydrochloride and sufficient excipient of lactose, starch, talc and magnesium stearate for a final weight of 100 mg.

PHARMACOLOGICAL STUDY (1) Affinities for the dopaminergic receptors

Striated bodies removed from the brains of 6 male rats weighing an average of 150 g were homogenized at one-twentieth (weight/volume) in 0.32M sucrose. After centrifuging the homogenized mixture at 1000 g for 10 minutes at 0° C., the supernatant was centrifuged at 30,000 g for 15 minutes at +4° C. The residue was taken up in 25 ml of Tris HCl 50 mM pH 7.7 buffer and centrifuged at 30,000 g for 15 minutes at +4° C. The new residue was taken up in 50 ml of Krebs Tris HCl pH 7.3 buffer and the suspension was pre-incubated for 10 minutes at 37° C. Then it was incubated for 29 minutes on a water-bath at +37° C. in the presence of spiroperidol $^3H$ alone, with an excess of haloperidol, and with increasing concentrations of the test product. The incubated suspensions were filtered on Whatman GF/C and the filters were washed three times with 5 ml of Tris HCl 50 mM buffer. The radioactivity of the filters is measured by liquid scintillation. The non-specific fixation was determined in parallel by incubation of spiroperidol $^3H$ in the presence of an excess of haloperidol. The affinity of the product tested for the dopaminergic receptors is given relative to haloperidol as reference product, CD = concentration of cold haloperidol inhibiting 50% of the specific fixation of the spiroperidol $^3H$, CX = concentration of the product under test inhibiting 50% of the specific fixation of the piroperidol $^3H$.

The relative affinity was determined by the relation:

$$RLA = 100 \frac{CD}{CX}$$

The following results were obtained:

| Test Product | Relative affinity (Haloperidol = 100) |
| --- | --- |
| Example 2 | 0.09 |
| Example 3 | 13 |
| Example 4 | 0.4 |

(2). Determination of hypotensive activity

The hypotensive activity was studied in male rats of WISTAR strain weighing about 300 g and anesthetized with nembutal (50 mg/kg by intraperitoneal route). The test product was administered intravenously in the jugular vein. The arterial pressure in the carotid was measured before and after administration of the test product. The following table indicates the variations expressed in percentage of the arterial pressure after administration of the product under test relative to the initial control arterial pressure.

| Product of Example | Dose mg/kg | % Variations of the arterial pressure 5 minutes after administration |
| --- | --- | --- |
| 2 | 1 | Variation of the arterial pressure between −30% and −40% |
| 3 | 0.1<br>0.01 | Variation of the arterial pressure beyond −40% |

(3) Antianoxic activity a—Test of hypobaric anoxia

Male mice weighing 20 to 22 g without food for 5 hours and arranged in groups of 10 animals were used. The product was administered to the animals subcutaneously and fifteen minutes after the administration of the product, the animals were placed in a 2 liter dessicator in which the pressure was taken rapidly to 190 mm Hg by a pump. The time of survival was noted, expressed in seconds and the increase in the time of survival was calculated for the treated animals relative to that of control animals submitted to the same conditions. The products of Examples 2, 3 and 4 were active respectively at a dose of 1 mg/kg, 0.01 mg/kg and 1 mg/kg.

b—Enolase test

Suffering cerebral cells release enolase γγ which is a specific indicator of neuronal lesions. In the test, the lesions were carried out in mice by subcutaneous injection of 35/mg/kg of kainic acid. The product of Example 3 administered intraperitoneally, upwards of a dose of 1 mg/kg, 1 hour after the injection of the neurotoxic, reduced the seral concentration of enolase which means the product protected the cerebral cells in the state of suffering.

(4) Study of the acute toxicity

The lethal doses $LD_0$ of the different compounds tested was evaluated after oral administration in mice and the maximal dose not causing any mortality over 8 days was called the $LD_0$. The following are the results obtained:

| Product to Example | $LD_0$ in mg/kg |
|---|---|
| 2 | >200 |
| 3 | 100 |

Various modifications of the compounds and method of the invention may be made without departing from the spirit or scope thereof and it should be understood that the invention is intended to be limited only as defined in the appended claims.

What we claim is:

1. A compound selected from the group consisting of tetrahydrobenz[c,d]indoles of the formula

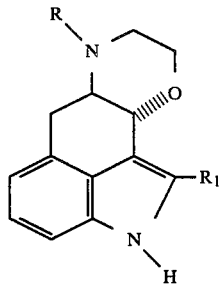

I wherein R is selected from the group consisting of hydrogen, alkyl of 1 to 6 carbon atoms and cycloalkyl of 3 to 6 carbon atoms and $R_1$ is selected from the group consisting of hydrogen, chlorine and bromine and their non-toxic, pharmaceutically acceptable acid addition salts.

2. A compound of claim 1 wherein $R_1$ is hydrogen.

3. A compound of claim 2 wherein R is hydrogen or linear alkyl of 1 to 6 carbon atoms.

4. A compound of claim 1 selected from the group consisting of (d,l-trans)-2,6a,7,8,9,10a-hexahydro-7-propyl-6H-indol-[4,3-g,h]-1,4-benzoxazine and its non-toxic, pharmaceutically acceptable acid addition salts.

5. A compound of claim 1 selected from the group consisting of (d,l-trans) 2,6a,7,8,9,10a-hexahydro-6H-indol-[4,3-g,h]-1,4-benzoxazine and its non-toxic, pharmaceutically acceptable acid addition salts.

6. A compound of claim 1 selected from the group consisting of (d,l-trans) 2,6a,7,8,9,10a-hexahydro-7-methyl-6H-indol-[4,3-g,h]-1,4-benzoxazine and its non-toxic, pharmaceutically acceptable acid addition salts.

7. A compound of the formula

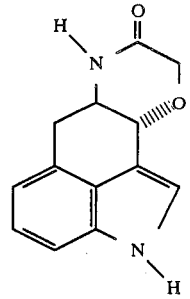

II

8. A antianoxic, hypotensive and dopaminergic agonist composition comprising an antianoxically, hypotensively, antihypertensively and dopaminergic agonistally effective amount of at least one compound of claim 1 and an inert pharmaceutical carrier.

9. A composition of claim 8 wherein $R_1$ is hydrogen.

10. A composition of claim 9 wherein R is hydrogen or linear alkyl of 1 to 6 carbon atoms.

11. A composition of claim 8 wherein the active compound is selected from the group consisting of (d,l-trans)-2,6a,7,8,9,10a-hexahydro-7-propyl-6H-indol-[4,3-g,h]-1,4-benzoxazine and its non-toxic, pharmaceutically acceptable acid addition salts.

12. A composition of claim 8 wherein the active compound is selected from the group consisting of (d,l-trans)-2,6a,7,8,9,10a-hexahydro-6H-indol-4[4,3 g,h]-1,4-benzoxazine and its non-toxic, pharmaceutically acceptable acid addition salts.

13. A composition of claim 8 wherein the active compound is selected from the group consisting of (d,l-trans) 2,6a,7,8,9,10a-hexahydro-7-methyl-6H-indol-[4,3-g,h]-1,4-benzoxazine and its non-toxic, pharmaceutically acceptable acid addition salts.

14. A method of inducing antianoxic, hypotensive, antihypertensive and dopaminergic agonist activity in warm-blooded animals comprising administering to warm-blooded animals an antianoxically, hypotensively, antihypertensively and dopaminergic agonistically effective amount of at least one compound of claim 1.

15. A method of claim 14 wherein $R_1$ is hydrogen.

16. A method of claim 15 wherein R is hydrogen or linear alkyl of 1 to 6 carbon atoms.

17. A method of claim 14 wherein the active compound is selected from the group consisting of (d,l-trans)-2,6a,7,8,9,10a-hexahydro-7-propyl-6H-indol-[4,3-g,h]-1,4-benzoxazine and its non-toxic, pharmaceutically acceptable acid addition salts.

18. A method of claim 14 wherein the active compound is selected from the group consisting of (d,l-trans)-2,6a,7,8,9,10a-hexahydro-6-H-indol-[4,3-g,h]-1,4-benzoxazine and its non-toxic, pharmaceutically acceptable acid addition salts.

19. A method of claim 14 wherein the active compound is selected from the group consisting of (d,l-trans)-2,6a,7,8,9,10a-hexahydro-7-methyl-6H-indol-[4,3-g,h]-1,4-benzoxazine and its non-toxic, pharmaceutically acceptable acid addition salts.

* * * * *